United States Patent [19]

Pressman et al.

[11] Patent Number: 5,908,952

[45] Date of Patent: *Jun. 1, 1999

[54] METHOD FOR PREPARING DIARYL CARBONATES EMPLOYING β-DIKETONE SALTS

[75] Inventors: Eric James Pressman, East Greenbush; Sheldon Jay Shafer, Clifton Park, both of N.Y.

[73] Assignee: General Electric Company, Schenectady, N.Y.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/823,784

[22] Filed: Mar. 24, 1997

[51] Int. Cl.⁶ .................................................... C07C 68/00
[52] U.S. Cl. ........................ 558/274; 558/271; 558/272; 558/273
[58] Field of Search .................... 558/274, 270, 558/271, 272, 273

[56] References Cited

U.S. PATENT DOCUMENTS

| 4,187,242 | 2/1980 | Chalk . |
| 5,231,210 | 7/1993 | Joyce et al. . |
| 5,284,964 | 2/1994 | Pressman et al. . |
| 5,399,734 | 3/1995 | King, Jr. et al. . |
| 5,502,232 | 3/1996 | Buysch et al. ........................ 558/270 |

FOREIGN PATENT DOCUMENTS

| 663388 | 7/1995 | European Pat. Off. . |
| 667336 | 8/1995 | European Pat. Off. . |
| 736512 | 9/1996 | European Pat. Off. . |
| 503581 | 9/1998 | European Pat. Off. . |

*Primary Examiner*—Michael G. Ambrose
*Attorney, Agent, or Firm*—Noreen C. Johnson; Douglas E. Stoner

[57] ABSTRACT

Hydroxyaromatic compounds such as phenol are converted to diaryl carbonates by reaction with oxygen and carbon monoxide in the presence of a catalyst package which comprises a Group VIIIB metal, preferably palladium, salt of at least one aliphatic β-diketone such as 2,4-pentanedione. The catalyst package also preferably comprises an inorganic cocatalyst, an organic cocatalyst and a bromide or chloride, preferably bromide, source such as a hexaalkylguanidinium bromide. The use of the β-diketone salt confers such advantages as long shelf life under normal storage conditions, high activity upon recycle and capability of carbonylation at relatively low temperatures.

18 Claims, No Drawings

METHOD FOR PREPARING DIARYL CARBONATES EMPLOYING β-DIKETONE SALTS

BACKGROUND OF THE INVENTION

This invention relates to the preparation of diaryl carbonates by carbonylation. More particularly, it relates to the improvement of shelf life and activity of the catalysts employed in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by a carbonylation reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst may be Group VIIIB metal compound, i.e., a compound of a metal selected from the group consisting of ruthenium, rhodium, palladium, osmium, iridium and platinum.

Further developments in the carbonylation reaction, including the use of palladium(II) acetate in combination with such cocatalysts as cobalt pentadentate complexes and terpyridines, are disclosed in U.S. Pat. Nos. 5,231,210, 5,284,964 and 5,399,734. These patents also disclose the use of quaternary ammonium or phosphonium halides, as illustrated by tetra-n-butylammonium bromide, as part of the catalyst package. The use of hexaalkylguanidinium chlorides or bromides in place of the quaternary salts is disclosed in copending provisional application Ser. No. 60/40,300.

The use of such Group VIIIB metal salts as the acetates is accompanied by certain disadvantages relating to the shelf life and activity of the catalyst mixture. It would be convenient to store the catalyst as a feed solution in the reactant hydroxyaromatic compound, said feed solution including the Group VIIIB metal salt in combination with at least one and preferably all of the other catalyst components. However, such feed solutions have extremely limited shelf life since the Group VIIIB metal precipitates therefrom on storage.

It would also be convenient to recycle the catalyst after use. Typically, the diaryl carbonate is recovered as an adduct with the hydroxyaromatic compound leaving the catalyst constituents in solution in further hydroxyaromatic compound. As noted herein-above, however, such solutions have very short shelf life.

Finally, temperatures for the carbonylation reaction on the order of 60–150° C. are disclosed in the aforementioned patents. It is generally found, however, that the divalent Group VIIIB metal acetates such as palladium(II) acetate afford diary carbonate in high yield only at temperatures in excess of about 100° C. Therefore, it would be desirable to employ a catalyst having a high degree of activity over a wider range of temperatures, including temperatures substantially below 100° C.

SUMMARY OF THE INVENTION

The present invention is based on the discovery of a series of Group VIIIB metal compounds which have numerous advantages when used as catalyst constituents in carbonylation. These advantages include long shelf life under normal storage conditions even in contact with reagent and other catalyst constituents, high activity upon recycle and capability of employment at relatively low temperatures.

The invention in one of its aspects is a method for preparing a diaryl carbonate which comprises contacting at least one hydroxyaromatic compound with oxygen and carbon monoxide in the presence of an amount effective for carbonylation of at least one catalytic material comprising a Group VIIIB metal salt of at least one aliphatic β-diketone.

Another aspect of the invention is storage stable catalyst compositions comprising a Group VIIIB metal salt of at least one aliphatic β-diketone, an inorganic cocatalyst, an organic cocatalyst and a chloride or bromide source, said composition being in solution in at least one hydroxyaromatic compound.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonates.

Other essential reagents in the method of this invention are oxygen and carbon monoxide, which react with the phenol to form the desired diaryl carbonate.

An essential constituent of the catalytic material employed according to the invention is a Group VIIIB metal salt of at least one aliphatic β-diketone. By "β-diketone" is meant a compound containing two keto carbonyl groups separated by a single carbon atom, usually but not necessarily in the form of a $CH_2$ linkage.

Suitable β-diketones include 2,4-pentanedione, 2,4-hexanedione and 3,5-heptanedione. The diketone salts of divalent metals are preferred, with the palladium(II) salt of 2,4-pentanedione being most preferred.

The catalytic material preferably also includes an inorganic cocatalyst of the type disclosed in the aforementioned U.S. Pat. No. 5,231,210 and/or an organic cocatalyst of the type disclosed in the aforementioned U.S. Pat. No. 5,284,964. It is preferred to employ both an inorganic and an organic cocatalyst.

Typical inorganic cocatalysts are complexes of cobalt(II) salts with organic compounds capable of forming complexes, especially pentadentate complexes, therewith. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkyl-ethylenediamines; crown ethers; aromatic or aliphatic amine ethers such as cryptanes; and Schiff bases. The especially preferred inorganic cocatalyst is a cobalt(II) complex with bis[3-(salicylalamino)propyl]methylamine, said complex hereinafter being designated "CoSMDPT".

Suitable organic cocatalysts include various terpyridine, phenanthroline, quinoline and isoquinoline compounds including 2,2':6',2"-terpyridine, 4'-methylthio-2,2':6',2"-terpyridine and 2,2':6',2"-terpyridine N-oxide, 1,10-phenanthroline, 2,4,7,8-tetramethyl-1,10-phenanthroline, 4,7-diphenyl-1,10,phenanthroline and 3,4,7,8-tetramethyl-1,10-phenanthroline. The terpyridines and especially 2,2':6', 2"-terpyridine are generally preferred.

The catalytic material also preferably contains a chloride or bromide, preferably bromide, source. It may be a quaternary ammonium or phosphonium salt, as disclosed in the afore-mentioned patents, or a hexaalkylguanidinium chloride or bromide as disclosed in copending provisional application Serial No. [RD-25209]. The guanidinium salts are often preferred; they include the α, w-bis(pentaalkylguanidinium)alkane salts. Salts in which the alkyl groups contain 2–6 carbon atoms and especially hexaethylguanidinium bromide are particularly preferred.

One important feature of the invention is the stability under storage conditions of the catalyst compositions, whether they include all or only some catalyst constituents. Thus, the palladium β-diketone salt may be stored in a single vessel in solution in the hydroxyaromatic compound and in combination with the inorganic cocatalyst, the organic cocatalyst and the chloride or bromide source. If it is more convenient to store various catalyst precursor compositions in separate batches, usually no more than two, that may also be done.

The proportion of Group VIIIB metal salt employed is an amount sufficient to provide about 1 gram-atom of metal per 800–10,000 and preferably 2,000–5,000 moles of hydroxyaromatic compound. For each gram-atom of Group VIIIB metal there is usually employed about 0.1–5.0 and especially about 0.5–1.5 gram-atoms of cobalt, about 0.1–3.0 and preferably about 0.3–1.0 moles of organic cocatalyst and about 5–150, preferably about 20–50, moles of chloride or bromide source.

Gas is supplied to the reaction mixture in proportions of about 2–50 mole percent oxygen, with the balance being carbon monoxide. The gases may be introduced separately or as a mixture, to a total pressure in the range of about 10–250 atmospheres. Reaction temperatures in the range of about 60–150° C. are typical, with temperatures in the range of about 80–110° and especially about 90–100° C. often being preferred by reason of decreased energy usage and the ability to employ gas proportions substantially lower in oxygen. Drying agents, typically molecular sieves, may be present in the reaction vessel. In order for the reaction to be as rapid as possible, it is preferred to maintain the reaction pressure in accordance with the aforementioned U.S. Pat. No. 5,399,734 until conversion of the hydroxyaromatic compound is complete.

The diaryl carbonates produced by the method of this invention may be isolated by conventional techniques. It is often preferred to form and thermally crack an adduct of the diaryl carbonate with the hydroxyaromatic compound, as described in U.S. Pat. Nos. 5,239,106 and 5,312,955.

The invention is illustrated by the following examples. All parts and proportions are by weight unless otherwise indicated. Proportions of reagents, though described as constant for all examples, varied in certain instances by reason of batch size approximation; however, experience has shown that such differences in proportions are not material with respect to product yield, conversion and the like.

EXAMPLE 1

A phenolic solution of palladium(II) 2,4-pentanedionate (500 ppm palladium) and 2,2':6',2"-terpyridine (0.33 equivalent) was placed in a 100-ml 3-necked round-bottomed flask fitted with a magnetic stirrer, nitrogen inlet and serum cap, and having a metal alloy coupon corresponding to a typical pressure reaction vessel suspended therein to simulate reactor conditions prior to carbonylation. The solution was clear and orange-yellow in color. It was heated at 60° C. under nitrogen, with stirring, for nine days, with samples periodically being removed for analysis. No precipitation or loss of soluble palladium was observed. By contrast, a control in which the palladium(II) 2,4-pentanedionate was replaced by an equivalent amount of palladium(II) acetate lost 33% of its palladium by precipitation over a period of seven days.

EXAMPLE 2

The procedure of Example 1 was repeated, except that the phenolic solution further contained 1 equivalent of CoSMDPT and 10 equivalents of hexaethylguanidinium bromide. No precipitation or loss of soluble palladium was observed after 21 days. By contrast, a control containing palladium(II) acetate lost 56% of its palladium by precipitation over seven days.

EXAMPLE 3

A constant composition gas flow reactor system, as disclosed in the aforementioned U.S. Pat. No. 5,399,734, was charged with 60.06 g (638 mmol) of phenol, 1001 mg (3.27 mmol) of hexaethylguanidinium bromide, 124.4 mg (0.303 mmol) of CoSMDPT, 23.9 mg (0.101 mmol) of 2,2':6',2"-terpyridine and 87.4 mg (0.288 mmol) of palladium(II) 2,4-pentanedionate (500 ppm palladium). Molecular sieves, 37 g, were placed in a perforated polytetrafluoroethylene basket mounted to the stir shaft of the reactor.

The reactor was sealed and heated to 110° C., with stirring, and a mixture of 12.8 mole percent oxygen and 87.2 mole percent carbon monoxide was introduced at a flow rate of 344 ml/min and a pressure of about 44 atmospheres. Gas flow was continued for 2 hours, after which a portion of the reaction mixture was removed and analyzed by high pressure liquid chromatography.

The reaction was repeated, employing a palladium(II) 2,4-pentanedionate-terpyridine combination which had been stored for 9 days as described in Example 1. As controls, reaction mixtures separately employing palladium(II) acetate, freshly prepared and stored for 7 days as described in Example 1, were employed. The results are given in Table I.

TABLE I

| Pd(II) Salt | Diphenyl carbonate yield, % |
|---|---|
| 2,4-Pentanedionate, fresh | 42.9 |
| 2,4-Pentanedionate, stored | 35.4 |
| Acetate, fresh | 43.3 |
| Acetate, stored | 14.0 |

The results in Table I show that the fresh 2,4-pentanedionate salt affords diphenyl carbonate in a yield comparable to that provided by the fresh acetate salt. After aging of the palladium salt, however, the yield afforded by the 2,4-pentanedionate salt is substantially higher than that of the control.

EXAMPLE 4

The procedure of Example 3 was repeated, using the catalyst composition of Example 2 diluted with phenol to the concentrations of catalyst constituents recited in Example 3. The yield of diphenyl carbonate was 38.4%. Thus, it is apparent that the catalyst compositions of the invention are storage stable.

EXAMPLE 5

A simulated carbonylation reaction mixture was prepared by incorporating the catalyst constituents described in Example 3 in a mixture of 42 parts of diphenyl carbonate and 58 parts of phenol, in the same proportions (i.e., 500 ppm palladium). The resulting homogeneous mixture was transferred to a stirred crystallizer maintained at 35° C. After several hours, the crystallized mixture was drained into a Buchner funnel at 35° C. and the diphenyl carbonate-phenol adduct was separated by filtration and washed with a homogeneous 10:90 diphenyl carbonate-phenol mixture.

The mother liquor was diluted with phenol to produce a mixture again containing 500 ppm of palladium, and said mixture was carbonylated as described in Example 3 except that the gas feed contained 9.1 mole percent oxygen. The yield of diphenyl carbonate after 2 hours was 51.5%, in comparison with 51.7% for a freshly prepared palladium(II) 2,4-pentanedionate-containing catalyst.

In control examples employing palladium(II) acetate as a catalyst constituent and an oxygen level of 12.8 mole percent, yields comparable to those using palladium(II) 2,4-pentanedionate were obtained with a freshly prepared catalyst. After separation of the diphenyl carbonate-phenol adduct, however, the yield using the recycled catalyst dropped to 42.4%. It is apparent, therefore, that the palladium(II) 2,4-pentanedionete catalyst mixture is more active than the palladium(II) acetate mixture upon recycling.

EXAMPLE 6

The procedure of Example 3 was repeated at various temperatures and oxygen levels, using both palladium(II) 2,4-pentanedionate and palladium(II) acetate as catalyst constituents. The results are given in Table II.

TABLE II

| Pd(II) salt | Temp. °C. | Oxygen, mole % | Diphenyl carbonate yield, % |
| --- | --- | --- | --- |
| 2,4-pentanedionate | 110 | 12.8 | 42.9 |
| 2,4-pentanedionate | 100 | 9.1 | 44.4 |
| 2,4-pentanedionate | 90 | 9.1 | 35.4 |
| 2,4-pentanedionate | 80 | 9.1 | 27.2 |
| Acetate | 110 | 12.8 | 43.3 |
| Acetate | 90 | 9.1 | 18.9 |

It is apparent that the 2,4-pentanedionate is a more active catalyst than the acetate at temperatures below 100° C.

What is claimed is:

1. A method for preparing a diaryl carbonate which comprises contacting at least one hydroxyaromatic compound with oxygen and carbon monoxide in the presence of an amount effective for carbonylation of at least one catalytic material comprising a hexaalkylguanidinium chloride or bromide and a Group VIIIB metal salt of at least one aliphatic β-diketone.

2. A method according to claim 1 wherein the Group VIIIB metal is palladium.

3. A method according to claim 2 wherein the palladium salt is palladium(II) 2,4-pentanedionate.

4. A method according to claim 3 wherein the hydroxyaromatic compound is phenol.

5. A method according to claim 2 wherein the catalytic material further comprises a cobalt(II) salt with an organic compound capable of forming a pentadentate complex.

6. A method according to claim 5 wherein the organic compound is bis[3-(salicylalamino)propyl]methylamine.

7. A method according to claim 2 wherein the catalytic material further comprises a terpyridine, phenanthroline, quinoline or isoquinoline compound as an organic cocatalyst.

8. A method according to claim 7 wherein the organic cocatalyst is 2,2':6',2"-terpyridine.

9. A method according to claim 2 wherein each alkyl group of the hexaalkylguanidinium bromide contains 2–6 carbon atoms.

10. A method according to claim 9 wherein the hexaalkylguanidinium bromide is hexaethylguanidinium bromide.

11. A method according to claim 2 wherein the proportions of oxygen and carbon monoxide are about 2–50 mole percent oxygen, with the balance being carbon monoxide.

12. A method according to claim 2 wherein the proportion of palladium is about 1 gram-atom per 2,000–5,000 moles of hydroxyaromatic compound.

13. A method according to claim 2 wherein about 0.5–1.5 gram-atoms of cobalt, about 0.3–1.0 mole of organic cocatalyst and about 20–50 moles of hexaalkylguanidinium halide are employed per gram-atom of palladium.

14. A storage stable composition comprising a Group VIIIB metal salt of at least one aliphatic β-diketone, a complex of a cobalt(II) salt as an inorganic cocatalyst, a terpyridine, phenanthroline, quinoline or isoquinoline compound as an organic cocatalyst and a hexaalkylguanidinium chloride or bromide, said composition being in solution in at least one hydroxyaromatic compound.

15. A composition according to claim 14 wherein the aliphatic β-diketone is 2,4-pentanedione.

16. A composition according to claim 15 wherein the inorganic cocatalyst is a cobalt(II) complex with bis[3-(salicylalamino)propyl]methylamine.

17. A composition according to claim 15 wherein the organic cocatalyst is 2,2':6',2"-terpyridine.

18. A composition according to claim 15 wherein the hexaalkylglanidinium chloride or bromide is hexaethylguanidinium bromide.

* * * * *